(12) United States Patent  
Lall et al.

(10) Patent No.: US 11,990,247 B1  
(45) Date of Patent: May 21, 2024

(54) INTEGRATED TELEMEDICINE SYSTEM

(71) Applicant: PHP LLC, Boca Raton, FL (US)

(72) Inventors: Hemindra Lall, Boca Raton, FL (US); Paul Schwartz, Boca Raton, FL (US); Paul Rosenberg, Boca Raton, FL (US)

(*) Notice: Subject to any disclaimer, the term of this patent is extended or adjusted under 35 U.S.C. 154(b) by 0 days.

(21) Appl. No.: 16/451,060

(22) Filed: Jun. 25, 2019

Related U.S. Application Data

(60) Provisional application No. 62/865,277, filed on Jun. 23, 2019, provisional application No. 62/689,479, filed on Jun. 25, 2018.

(51) Int. Cl.
| | | |
|---|---|---|
| *G16H 80/00* | (2018.01) | |
| *G16H 10/60* | (2018.01) | |
| *G16H 15/00* | (2018.01) | |
| *G16H 20/10* | (2018.01) | |
| *G16H 40/20* | (2018.01) | |

(52) U.S. Cl.  
CPC ............ *G16H 80/00* (2018.01); *G16H 10/60* (2018.01); *G16H 20/10* (2018.01); *G16H 40/20* (2018.01); *G16H 15/00* (2018.01)

(58) Field of Classification Search  
CPC ........ G16H 10/60; G16H 15/00; G16H 20/10; G16H 40/20; G16H 80/00  
See application file for complete search history.

(56) References Cited

U.S. PATENT DOCUMENTS

| | | | |
|---|---|---|---|
| 2006/0106290 A1* | 5/2006 | Bulat | A61B 5/0002 600/300 |
| 2008/0065414 A1* | 3/2008 | Schoenberg | G16H 10/20 705/2 |
| 2013/0064358 A1* | 3/2013 | Nusbaum | H04M 3/42068 379/88.16 |
| 2015/0025902 A1* | 1/2015 | Wasson | G16H 10/60 705/2 |

(Continued)

OTHER PUBLICATIONS

P. de Toledo, S. Jimenez, F. del Pozo, J. Roca, A. Alonso and C. Hernandez, "Telemedicine Experience for Chronic Care in COPD," in IEEE Transactions on Information Technology in Biomedicine, vol. 10, No. 3, pp. 567-573, Jul. 2006. (Year: 2006).*

*Primary Examiner* — Mamon Obeid  
*Assistant Examiner* — Chance L Smith  
(74) *Attorney, Agent, or Firm* — Wayne Edward Ramage; Baker Donelson

(57) ABSTRACT

A medical answering service, typically live and telephonically-based, integrated with a cloud-based telemedicine model using HIPPA compliant and encrypted communications technology to provide e-Visits between physician/providers and patients. The system provides the physician 20 or healthcare provider with a unique DID/phone number for their practice, as well as applicable software applications (and hardware, if required) for installation or integration with a phone dialer, texting/SMS applications, and/or email client for later contact and use. A patient calling the unique DID/phone number is received and triaged by the system, (Continued)

which coordinates an e-Visit in a virtual room. The e-Visit may include real time patient measurements taken from remote peripheral devices. System communications with the physician/provider and patient are conducted using up to 4 independent channels of communication.

8 Claims, 7 Drawing Sheets

(56) References Cited

U.S. PATENT DOCUMENTS

| | | | |
|---|---|---|---|
| 2015/0278453 A1* | 10/2015 | Joao | G16H 80/00 |
| | | | 705/3 |
| 2017/0116384 A1* | 4/2017 | Ghani | G16H 10/60 |
| 2017/0323074 A1* | 11/2017 | Chiang | H04N 7/147 |
| 2018/0330063 A1* | 11/2018 | Viswanathan | G16H 80/00 |
| 2020/0066414 A1* | 2/2020 | Neff | H04L 12/1818 |

\* cited by examiner

INTEGRATED TELEMEDICINE SYSTEM

This application claims benefit of and priority to U.S. Provisional Applications No. 62/689,479, filed Jun. 25, 2018, and No. 62/865,277, filed Jun. 23, 2019, both of which are incorporated herein in their entireties by specific reference for all purposes.

FIELD OF INVENTION

This invention relates to a system and methods for providing a medical answering service integrated with a telemedicine platform. More particularly, the present invention relates to a system and methods for providing a medical answering service to manage and coordinate delivery of tele-healthcare through an integrated, cloud-based telemedicine platform that directly connects physicians and caregivers with patients in real time.

SUMMARY OF INVENTION

In various exemplary embodiments, the present invention comprises a medical answering service, typically live and telephonically-based, integrated with a cloud-based telemedicine model using HIPPA compliant and encrypted communications technology. The system allows healthcare providers/physicians to securely connect with and manage medical conditions of patients without the issues and cumbersomeness of a separate, dedicated telemedicine system. An around-the-clock coordination hub allows the system to locate particular providers for an unscheduled patient caller and establish a telemedicine event, anytime and anywhere, in real time.

In several embodiments, the physician or other healthcare provider initially signs up for the custom telehealth integrated telehealth/telemedicine service. The provider provides practice information (e.g., type and nature of practice), contact information, and other relevant information, which are stored by the system's administrative software and database. The system provides the physician or healthcare provider with a unique DID (direct inward dialing)/phone number for their practice, as well as applicable software applications (and hardware, if required) for installation or integration with a phone dialer, texting/SMS applications, and/or email client for later contact and use.

A patient calls their physician's answering service provided by the system using the unique DID/phone number. The system identifies the physician or healthcare provider for that patient call based upon the provider DID used, and where possible, identifies the patient based upon the provider DID and the patient phone number stored in the system database. The operator answers the call, greeting the patient appropriately based upon the information provided by the practice at the time of signing up or obtained thereafter. The patient may request a standard telephone call with the physician, or a virtual telehealth consult. The operator may triage the patient. If any co-pay or administrative task needs to be done, depending on the request, the operator executes those tasks before or while a virtual telehealth consult is being sent to the physician/provider.

Once the patient is cleared by the operator, and the physician/provider has indicated availability for the virtual visit, a link is sent via text, email and/or other forms of communication to both the physician/provider and the patient. If any information has been collected from the patient during triage, the operator provides that information to the physician/provider when the link is sent. The physician/provider and the patient click on their respective links with their respective devices to enter the virtual telehealth consult. The device can be a computer or laptop with a web browser, a telephone with videoconferencing capability, a smart phone, a tablet, or other form of computing or mobile computing device.

The operator remains on standby until both the provider and patient are in the virtual room and the virtual face-to-face visit has been initiated. Once the visit is established, the operator may then drop out of the transaction. The physician/provider then conducts a telemedicine consult or visit with the patient, which may include directing the patient to use equipment or sensors at home to allow the physician/provider to examine and diagnose the patient remotely in real time.

DETAILED DESCRIPTION OF EXEMPLARY EMBODIMENTS

Figure 1:
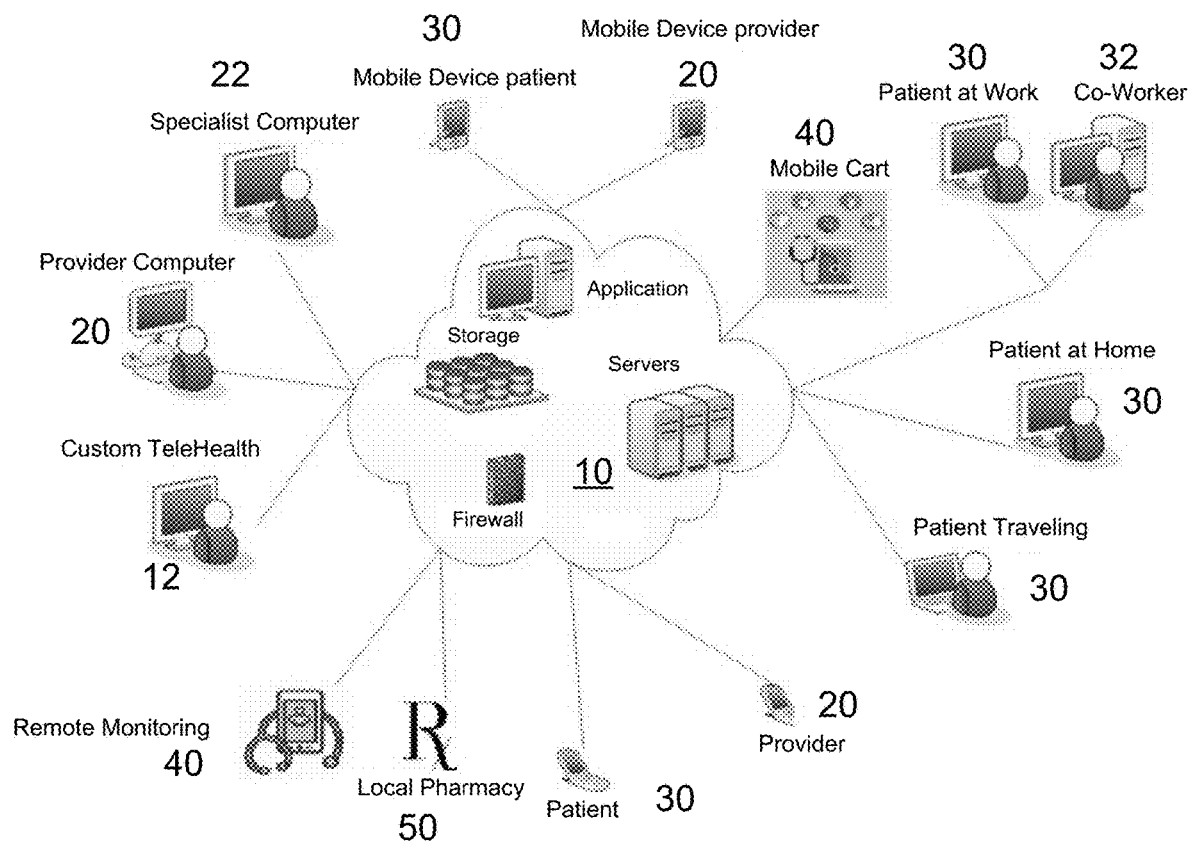
FIG. 1 shows a diagram of a system in accordance with an exemplary embodiment of the present invention.

In various exemplary embodiments, the present invention comprises a medical answering service, typically live and telephonically-based, integrated with a cloud-based telemedicine model using HIPPA compliant and encrypted communications technology. The system allows healthcare providers/physicians 20 and consulting providers and/or specialists 22 to securely connect with and manage medical conditions of patients 30 without the issues and cumbersomeness of a separate, dedicated telemedicine system. An around-the-clock coordination hub 10 (which may include a telemedicine coordinator or operator 12) allows the system to locate particular providers 20, 22 for an unscheduled patient caller and establish a telemedicine event, anytime and anywhere, in real time. Multiple users (such as a patient 30 and a fellow co-worker at the same location who is also a patient 32) may log in or call into the system simultaneously from a single location using a single line or different lines, or from multiple locations.

In various embodiments, the physician 20 or other healthcare provider initially signs up for the custom telehealth integrated telehealth/telemedicine service. The provider provides practice information (e.g., type and nature of practice), contact information, and other relevant information, which are stored by the system's central administrative software and database 10. The system provides the physician 20 or healthcare provider with a unique DID/phone number for their practice, as well as applicable software applications (and hardware, if required) for installation or integration with a phone dialer, texting/SMS applications, and/or email client for later contact and use.

Figure 2:
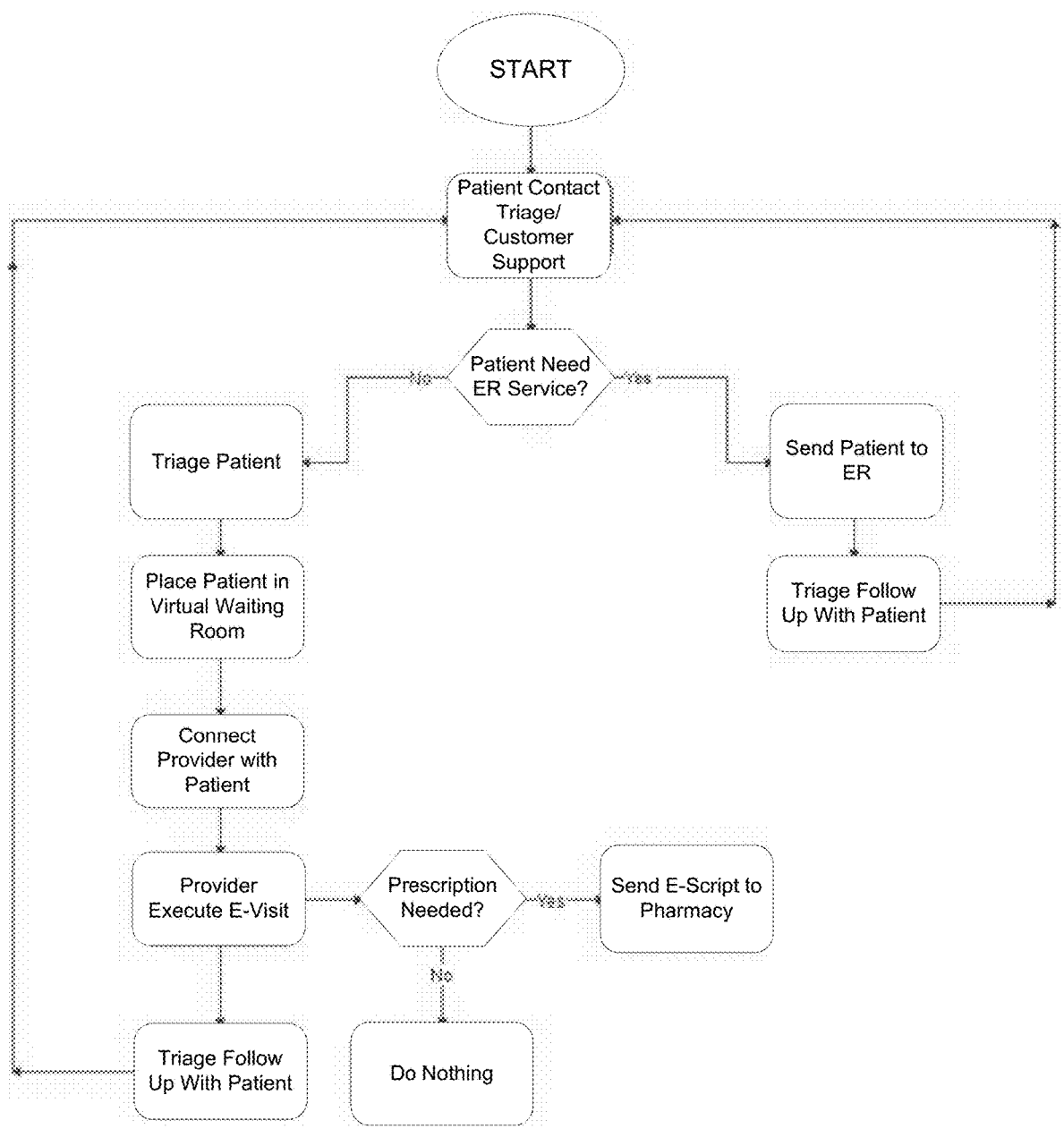
FIG. 2 shows a diagram of a method in accordance with an exemplary embodiment of the present invention.

In one exemplary embodiment, a process in accordance with the present invention comprises the following steps, as seen in FIG. 2. A patient 30 calls their physician's office using the physician's office number where it is routed using the unique DID/phone number to the answering service (provided by the system). Alternatively, the physician's office forwards the call to the answering service using the unique DID/phone number or other number provided by the system (such as for a new patient intake or follow-up service). In a further alternative embodiment, the patent calls the physician's answering service using the unique DID/phone number directly. Prior to a telemedicine coordinator or operator 12 answering the call, the system identifies the physician or healthcare provider for that patient call based upon the provider DID used, and where possible, identifies the patient based upon the provider DID and the patient phone number stored in the system database.

The telemedicine coordinator/operator answers the call, greeting the patient 30 appropriately based upon the information provided by the practice at the time of signing up or obtained thereafter. The patient 30 may request a standard telephone call with the physician 20, or a virtual telehealth consult. The telemedicine coordinator/operator may triage the patient. If any co-pay or administrative task needs to be done, depending on the request, the telemedicine coordinator/operator executes those tasks before or while a virtual telehealth consult request is being sent to the physician/provider 20.

Once the patient 30 is cleared by the telemedicine coordinator/operator, and the physician/provider 20 has indicated availability for the virtual visit, the system transmits information for the virtual telehealth consult (i.e., e-Visit) using up to four methods or channels of communication simultaneously. The coordinator may send an email, eFax, SMS text, and a video conferencing link to both patient and physician/provider. The patent may download the e-Visit application to his or her device, if needed. The system provides confirmation to the coordinator of receipt by the patient and physician/provider, ensuring that both patient and physician/provider acknowledge the messaging, and ensuring that the e-Visit time and date, along with all other relevant information (such as information collected from the patient during triage), is provided to the parties that are participating in the e-Visit. The physician/provider and the patient may respond to the coordinator using any of these four channels of communication on any device, so that a communication may be received on one channel, with a responsive communication sent on another channel. All communication methods are device independent, bidirectional and cross-platform. The same methods of multiple simultaneous communication channels may be used to have additional providers and specialist associates present in the e-Visit, if needed for a second opinion or consult.

The physician/provider and the patient click on their respective links with their respective devices to enter the virtual telehealth consult. The device can be a computer or laptop with a web browser, a telephone with videoconferencing capability, a smart phone, a tablet, or other form of computing or mobile computing device.

The coordinator remains on standby until both the physician/provider and patient are in the virtual room and the virtual e-Visit has been initiated. Once the e-Visit is established, the coordinator may then drop out of the transaction. The physician/provider then conducts a telemedicine consult or visit with the patient, which may include directing the patient to use equipment or sensors at home to allow the physician/provider to examine and diagnose the patient remotely in real time (e.g., the patient may apply a remote stethoscope with sound or sensor readings being sent electronically to the physician/provider in real time), or the addition of another provider and/or specialist associate, if needed for a second opinion or consult.

Remote monitoring systems with equipment and sensors 40 may be in the patient's home, a caregiver's home, or a healthcare facility, or other locations, in which the patient resides or is located. Healthcare facilities include, but are not limited to, skilled nurse facilities or assisted living facilities. Remote monitoring systems include, but are not limited to, mobile carts, mobile cases, concierge kits, and other forms of remote monitoring platforms. In several embodiments, remote monitoring systems comprise bidirectional communications that are cross-platform and is independent of particular operating systems. All peripheral data from the patient may be transmitted via Bluetooth or wireless communications to the patient device and then to the central system. Such measurements may be taken as part of an e-Visit, or separately from an e-Visit. Information and alerts from the equipment, sensors or other devices may be transmitted to the physician/provider using the multiple simultaneous communication channels discussed above.

The system thus provides a medical concierge service whereby patients contact the system's communication hub using a specific number provided by their physician/provider, and thereby conduct a telemedicine consultation meeting (e-Visit) directly with their own physician/provider. The system connects a physician/provider directly with their patient for an e-Visit in real time using an integrated answering service (available around the clock) with a coordination hub and cross-platform telemedicine system. No existing telemedicine system or platform connects a physician with their patient in real-time around the clock.

In additional embodiments, a general number can be provided for general consultation or calls, where the system can receive and triage calls, and match a caller with a physician or other healthcare provider, if requested.

The system may vary depending on the nature of the healthcare provider. FIG. 2 shows an example of the system for a patient call to a hospital/nursing home/emergency room (ER), which is routed or directed to the system using the unique DID/phone number as described above, or for a call from a hospital/nursing home/emergency room regarding a or on behalf of patient. If the patient is not at the facility, the patient is initially triaged to determine if an emergency exists. If so, the patient is directed to call 911 and go to the ER, with later follow-up. If no, the patient is further triaged and placed in a virtual waiting room. The patient's physician or provider is connected, and executes an e-Visit with diagnosis and treatment (including the physician or provider sending the patient to the ER if deemed necessary), with later follow-up. For example, if a prescription is needed, an e-script is sent to a local pharmacy 50.

Figure 3:
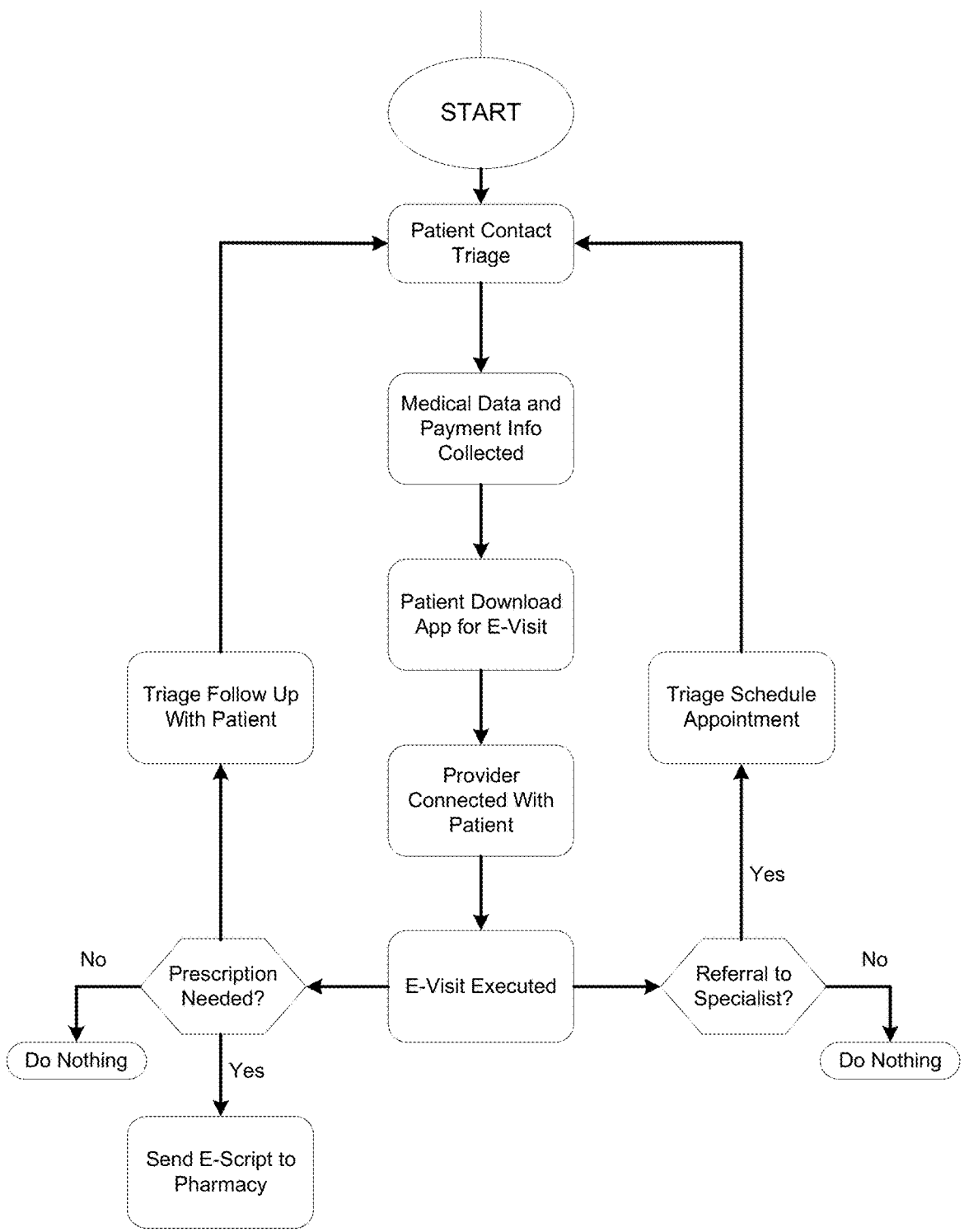
FIG. 3 shows a diagram of another method in accordance with an exemplary embodiment of the present invention.

FIG. 3 shows an example of the system as described above, with the patient calling from their home or other location. The patient is triaged as discussed above, with collection of medical data and payment/insurance information. As noted, the patient downloads the appropriate device application for the e-Visit if this is the first time using the e-Visit system or using a particular device (otherwise, the patient will use the already downloaded application on their computer or mobile device). The e-Visit is conducted, which may result in further follow-up, a prescription being provided, or referral to a specialist.

Figure 4:
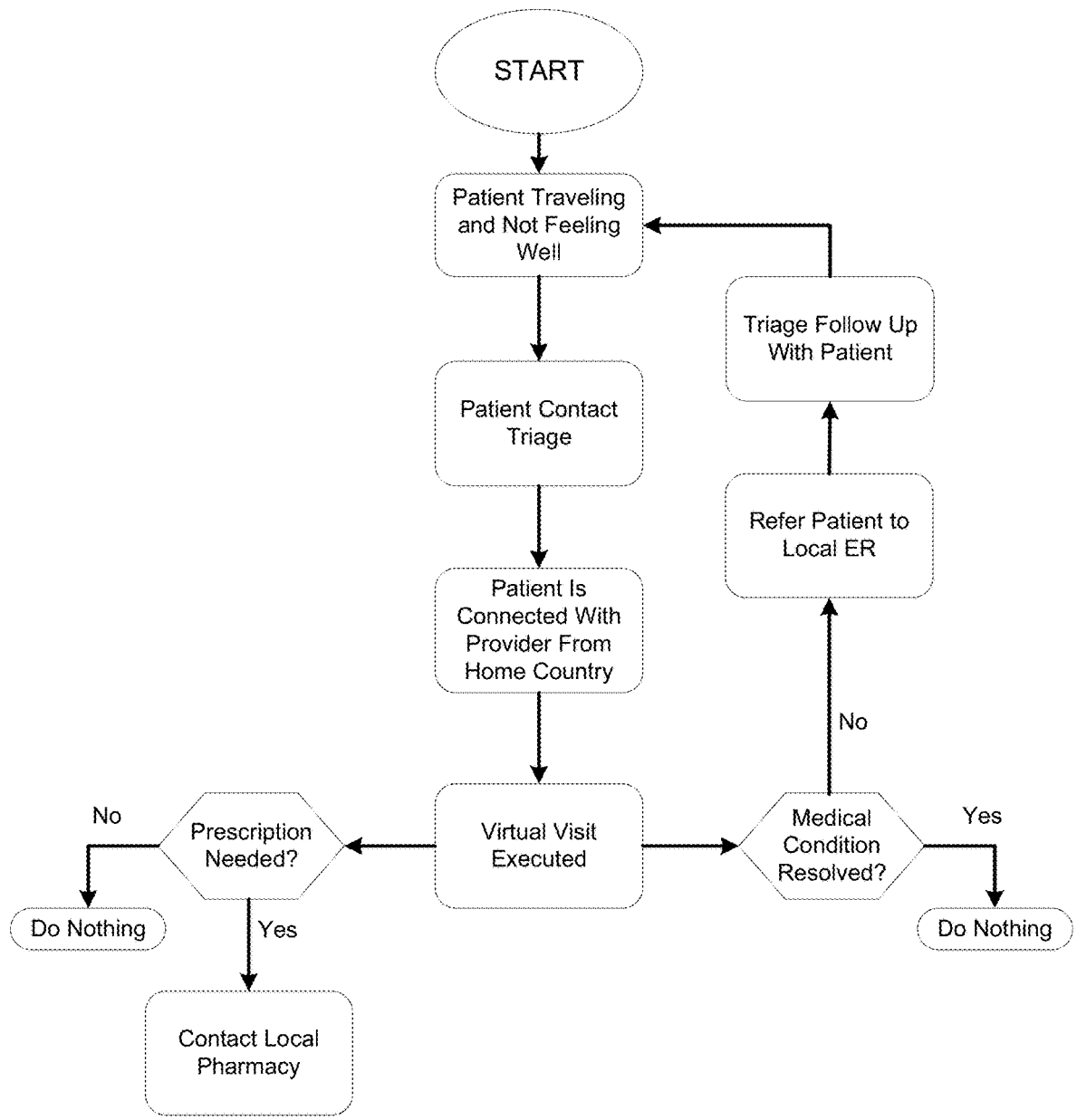
FIG. 4 shows a diagram of another method in accordance with an exemplary embodiment of the present invention.

FIG. 4 shows an example of the system as described above, with the patient traveling overseas. The patient may enter the system using a local telephone number, or dial the physician/provider DID as an international call. The e-Visit is conducted with the patient's physician/provider as described above, and also may result in appropriate follow-up, or a prescription or referral locally.

Figure 5:
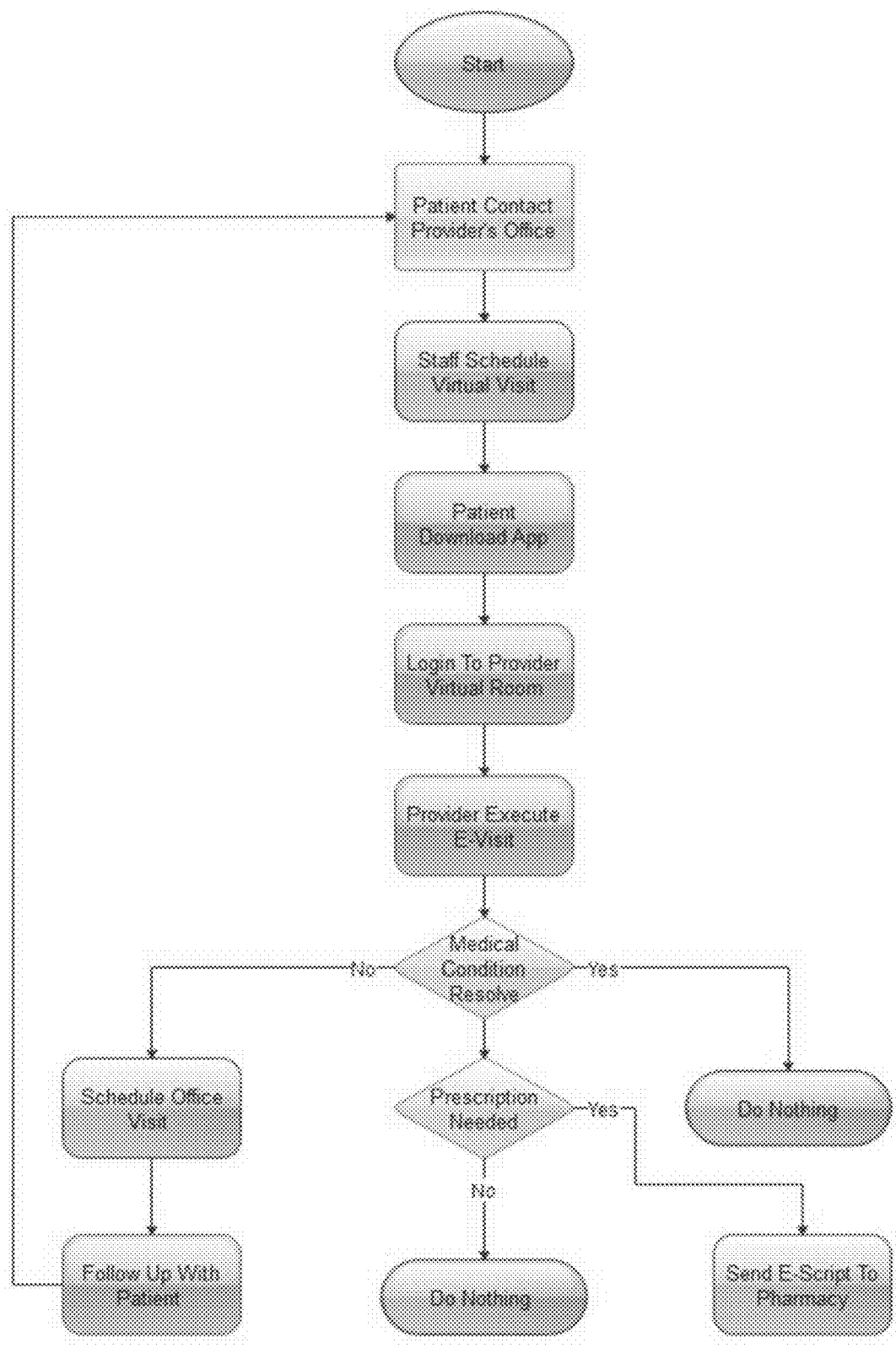
FIG. 5 shows a diagram of another method in accordance with an exemplary embodiment of the present invention.

FIG. 5 shows an example of the system as described above, with the patient directly contacting the physician/provider's office. This assumes that there is still at least one staff person in the office answering calls, so that patient has not called the physician's answering service (provided by the system) using the unique DID/phone number. The staff person answering the call then logs into the system and schedules an e-Visit between the patient and their physician/provider. The patient downloads the application program (if necessary). The system then arranges for the e-Visit with multiple-channel communication as described above, with the patient and provider entering or logging into the e-Visit virtual room where the e-Visit is executed as discussed above. The physician/provider may bring another provider or specialist into the e-Visit, schedule a follow-up in-office visit with the patient, provide a prescription (i.e., send an e-Script to a pharmacy), or take other appropriate action, such as referring the patient to another provider or specialist, or refer the patient to an emergency room or emergency care provider.

Figure 6:
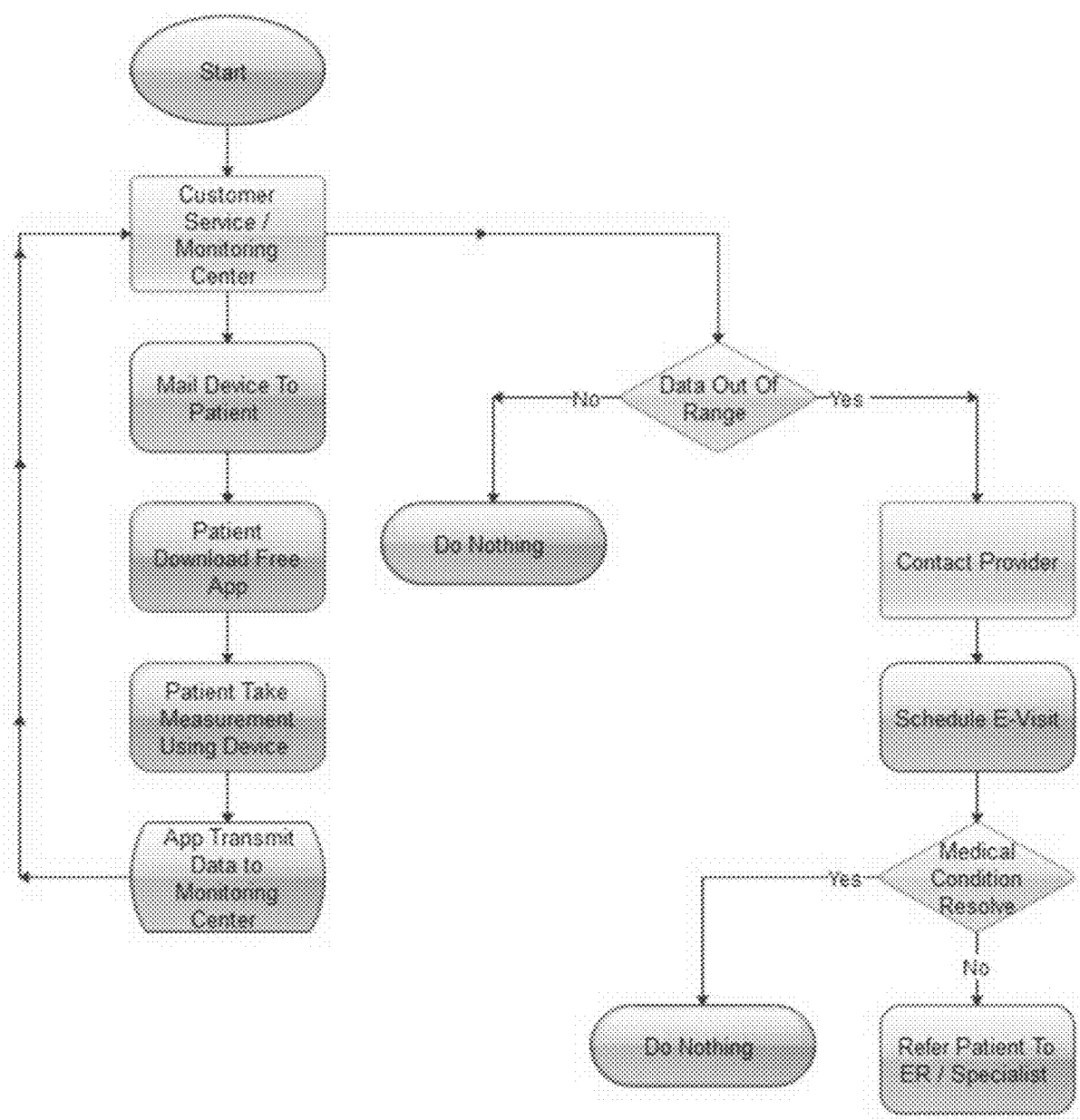
FIG. 6 shows a diagram of another method in accordance with an exemplary embodiment of the present invention.

FIG. 6 shows an example of the system as a remote monitoring center, with the patient using a device to take a health-care related measurement (e.g., temperature, blood pressure). The central system (customer service/monitoring center) may arrange to mail or otherwise provide the necessary devices to the patient. The patient may download the necessary application to their computer or mobile device to interface with the system, and also operate and/or communicate with the device(s). The patient uses the device or devices to take appropriate measurements at appropriate times or intervals as determined by his or her physician/provider, and the application transmits the measurement data to the system monitoring center. In various embodiments, the system monitoring center forwards the data to the physician/provider. If the data is not within a pre-determined range set by the physician/provider, exceeds or falls below pre-determined thresholds set by the physician/provider, or falls outside sampling windows (i.e., transmitted early or late, or not transmitted at all), then the system alerts the physician/provider of the "out of range" data value or values, along with providing at least the data causing the alert. The physician/provider may desire to arrange an e-Visit, and directs the system to schedule an e-Visit with the patient. The e-Visit is conducted as discussed above, and the physician/provider may bring another provider or specialist into the e-Visit, refer the patient to another provider or specialist, or refer the patient to an emergency room or emergency care provider.

Figure 7:
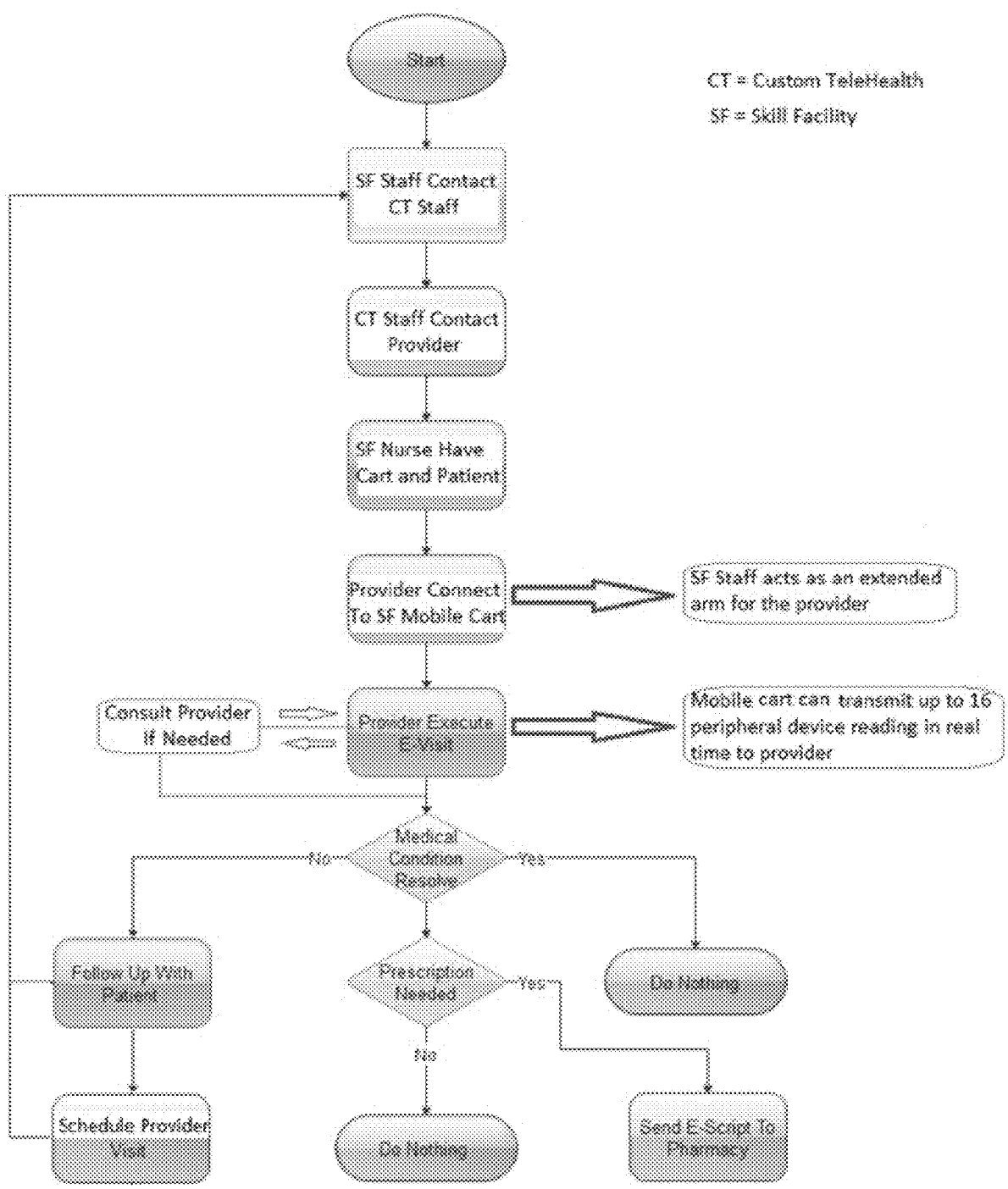
FIG. 7 shows a diagram of another method in accordance with an exemplary embodiment of the present invention.

FIG. 7 shows an example of the system with the patient located at a healthcare facility as described above (in this embodiment, a skilled nurse facility), with facility staff interacting with the patient to effectively act as an "extended arm" of the physician/provider in an e-Visit as described above. The facility staff contacts the telehealth system, which then contacts the physician/provider and provides the e-Visit information to the parties as described above. In the embodiment shown, the facility has a mobile cart capable of transmitting readings from up to 16 peripheral devices in real time to the physician/provider. The physician/provider connects to the mobile cart, and the e-Visit is executed as described above (e.g., additional providers or specialists may be added to the e-Visit, and so on). The resolution of the e-Visit also is as described above, with possible referrals, prescriptions, and follow-ups (such as scheduling a in-person visit with the provider and patient at the provider's office or at the facility).

In order to provide a context for the various computer-implemented aspects of the invention, the following discussion provides a brief, general description of a suitable computing environment in which the various aspects of the present invention may be implemented. A computing system environment is one example of a suitable computing environment, but is not intended to suggest any limitation as to the scope of use or functionality of the invention. A computing environment may contain any one or combination of components discussed below, and may contain additional components, or some of the illustrated components may be absent. Various embodiments of the invention are operational with numerous general purpose or special purpose computing systems, environments or configurations. Examples of computing systems, environments, or configurations that may be suitable for use with various embodiments of the invention include, but are not limited to, personal computers, laptop computers, computer servers, computer notebooks, hand-held devices, microprocessor-based systems, multiprocessor systems, TV set-top boxes and devices, programmable consumer electronics, cell phones, personal digital assistants (PDAs), tablets, smart phones, touch screen devices, smart TV, internet enabled appliances, internet enabled security systems, internet enabled gaming systems, internet enabled watches; internet enabled cars (or transportation), network PCs, minicomputers, mainframe computers, embedded systems, virtual systems, distributed computing environments, streaming environments, volatile environments, and the like.

Embodiments of the invention may be implemented in the form of computer-executable instructions, such as program code or program modules, being executed by a computer, virtual computer, or computing device. Program code or modules may include programs, objects, components, data elements and structures, routines, subroutines, functions and the like. These are used to perform or implement particular tasks or functions. Embodiments of the invention also may be implemented in distributed computing environments. In such environments, tasks are performed by remote processing devices linked via a communications network or other data transmission medium, and data and program code or modules may be located in both local and remote computer storage media including memory storage devices such as, but not limited to, hard drives, solid state drives (SSD), flash drives, USB drives, optical drives, and internet-based storage (e.g., "cloud" storage).

In one embodiment, a computer system comprises multiple client devices in communication with one or more server devices through or over a network, although in some cases no server device is used. In various embodiments, the network may comprise the Internet, an intranet, Wide Area Network (WAN), or Local Area Network (LAN). It should be noted that many of the methods of the present invention are operable within a single computing device.

A client device may be any type of processor-based platform that is connected to a network and that interacts with one or more application programs. The client devices each comprise a computer-readable medium in the form of volatile and/or nonvolatile memory such as read only memory (ROM) and random access memory (RAM) in communication with a processor. The processor executes computer-executable program instructions stored in memory. Examples of such processors include, but are not limited to, microprocessors, ASICs, and the like.

Client devices may further comprise computer-readable media in communication with the processor, said media storing program code, modules and instructions that, when executed by the processor, cause the processor to execute the program and perform the steps described herein. Computer readable media can be any available media that can be accessed by computer or computing device and includes both volatile and nonvolatile media, and removable and non-removable media. Computer-readable media may further comprise computer storage media and communication media. Computer storage media comprises media for storage of information, such as computer readable instructions, data, data structures, or program code or modules. Examples of computer-readable media include, but are not limited to, any electronic, optical, magnetic, or other storage or transmission device, a floppy disk, hard disk drive, CD-ROM, DVD, magnetic disk, memory chip, ROM, RAM, EEPROM, flash memory or other memory technology, an ASIC, a configured processor, CDROM, DVD or other optical disk storage, magnetic cassettes, magnetic tape, magnetic disk storage or other magnetic storage devices, or any other medium from which a computer processor can read instructions or that can store desired information. Communication media comprises media that may transmit or carry instructions to a computer, including, but not limited to, a router, private or public network, wired network, direct wired connection, wireless network, other wireless media (such as acoustic, RF, infrared, or the like) or other transmission device or channel. This may include computer readable instructions, data structures, program modules or other data in a modulated data signal such as a carrier wave or other transport mechanism. Said transmission may be wired, wireless, or both. Combinations of any of the above should also be included within the scope of computer readable media. The instructions may comprise code from any computer-programming language, including, for example, C, C++, C#, Visual Basic, Java, and the like.

Components of a general purpose client or computing device may further include a system bus that connects various system components, including the memory and processor. A system bus may be any of several types of bus structures, including, but not limited to, a memory bus or memory controller, a peripheral bus, and a local bus using any of a variety of bus architectures. Such architectures include, but are not limited to, Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computing and client devices also may include a basic input/output system (BIOS), which contains the basic routines that help to transfer information between elements within a computer, such as during start-up. BIOS typically is stored in ROM. In contrast, RAM typically contains data or program code or modules that are accessible to or presently being operated on by processor, such as, but not limited to, the operating system, application program, and data.

Client devices also may comprise a variety of other internal or external components, such as a monitor or display, a keyboard, a mouse, a trackball, a pointing device, touch pad, microphone, joystick, satellite dish, scanner, a disk drive, a CD-ROM or DVD drive, or other input or output devices. These and other devices are typically connected to the processor through a user input interface coupled to the system bus, but may be connected by other interface and bus structures, such as a parallel port, serial port, game port or a universal serial bus (USB). A monitor or other type of display device is typically connected to the system bus via a video interface. In addition to the monitor, client devices may also include other peripheral output devices such as speakers and printer, which may be connected through an output peripheral interface.

Client devices may operate on any operating system capable of supporting an application of the type disclosed herein. Client devices also may support a browser or browser-enabled application. Examples of client devices include, but are not limited to, personal computers, laptop computers, personal digital assistants, computer notebooks, hand-held devices, cellular phones, mobile phones, smart phones, pagers, digital tablets, Internet appliances, and other processor-based devices. Users may communicate with each other, and with other systems, networks, and devices, over the network through the respective client devices.

Thus, it should be understood that the embodiments and examples described herein have been chosen and described in order to best illustrate the principles of the invention and its practical applications to thereby enable one of ordinary skill in the art to best utilize the invention in various embodiments and with various modifications as are suited for particular uses contemplated. Even though specific embodiments of this invention have been described, they are not to be taken as exhaustive. There are several variations that will be apparent to those skilled in the art.

What is claimed is:

1. A telemedicine system, comprising:
an integrated medical answering service and telemedicine system, comprising a coordination hub with a plurality of remote servers in electronic communication with one or more storage devices with a database, a plurality of physician and/or healthcare provider computing devices, a plurality of physician and/or healthcare provider mobile computing devices, and one or more healthcare remote monitoring devices, over a telecommunications network;
and at least one microprocessor associated with at least one of said plurality of remote servers, wherein said at least one microprocessor is programmed to:
receive, over the telecommunications network, information from a physician or healthcare provider to enroll the physician or healthcare provider in the integrated medical answering service;
automatically generate a unique direct inward dialing phone number for each enrolled physician or healthcare provider;
provide, over the telecommunications network, the unique direct inward dialing phone number to the enrolled physician or healthcare provider;
receive, over the telecommunications network from a physician or healthcare provider computing device, patient information from one or more patients of the physician or healthcare provider, said patient information comprising a patient number;
store said patient information in the database;
receive, over the telecommunications network from a caller mobile computing device or telephone, an incoming call from a caller on a caller number to a particular unique direct inward dialing phone number;
prior to the incoming call being answered, identify the physician or healthcare provider associated with the particular unique direct inward dialing phone number;

prior to the incoming call being answered, determine whether the caller number matches a patient number in the database, and if a match is found, identify the patient associated with the incoming call;

transmit over the telecommunications network the physician or healthcare provider identification and the patient identification, if available, to a telemedicine coordinator;

direct the incoming call to the telemedicine coordinator;

present the caller with the option to request a virtual telehealth consult or request a standard telephone call;

in response to a request for a virtual telehealth consult, electronically transmit over the telecommunications network a virtual telehealth consult to a computing device of the physician or healthcare provider, wherein the virtual telehealth consult request is separate from and independent of the call;

if an acceptance message for the virtual telehealth consult request is received over the telecommunications network from the computing device of the physician or healthcare provider, electronically transmit over the telecommunications network information for the virtual telehealth consult to both the patient and the physician or healthcare provider; and initiate the virtual telehealth consult, wherein the virtual telehealth consult is separate from and independent of the call; and further wherein the virtual telehealth consult comprises a real-time electronic video communication over the telecommunications network through a first computing device of the physician or healthcare provider and a second computing device of the patient, the first computing device being remote from the second computing device, each computing device configured with a camera and microphone to record and transmit an audio-visual data stream originating with the respective computing device, and each computing device configured with a display configured to display in real time the audio-visual data stream transmitted by the other computing device;

wherein the patient is a pre-existing patient of the physician or healthcare provider.

2. The system of claim 1, further wherein the microprocessor is programmed to:

electronically transmit a request to join the virtual telehealth consult to one or more additional physicians or health care providers.

3. The system of claim 1, wherein the virtual telehealth consult comprises the transmission of healthcare data regarding the patient from a remote monitoring system.

4. The system of claim 3, wherein the remote monitoring system comprises a mobile cart with one or more peripheral healthcare data devices.

5. The system of claim 3, wherein the healthcare data is collected during the virtual telehealth consult and transmitted in real time.

6. The system of claim 1, wherein the virtual telehealth consult request to the physician or healthcare provider is sent simultaneously over two or more electronic communications channels.

7. The system of claim 6, wherein the virtual telehealth consult request to the physician or healthcare provider is sent simultaneously over four electronic communications channels.

8. The system of claim 6, wherein the two electronic communications channels comprise an email, eFax, and/or SMS text.

* * * * *